United States Patent [19]

Abdulwahed et al.

[11] Patent Number: 6,037,304

[45] Date of Patent: Mar. 14, 2000

[54] HIGHLY ACTIVE AND SELECTIVE CATALYSTS FOR THE PRODUCTION OF UNSATURATED NITRILES, METHODS OF MAKING AND USING THE SAME

[75] Inventors: Mazhar Abdulwahed, Syria, Syrian Arab Rep.; Khalid El Yahyaoui, Meknes, Morocco

[73] Assignee: Saudi Basic Industries Corporation, Saudi Arabia

[21] Appl. No.: 09/228,885

[22] Filed: Jan. 11, 1999

[51] Int. Cl.[7] .............. B01J 23/00; B01J 23/32; B01J 23/02; B01J 23/16

[52] U.S. Cl. ............. 502/300; 502/305; 502/306; 502/312; 502/313; 502/319; 502/321; 502/324; 502/340; 502/325; 502/353

[58] Field of Search .............. 502/300, 311, 502/305, 306, 312, 313, 319, 321, 324, 325, 340, 353

[56] References Cited

U.S. PATENT DOCUMENTS

| | | | |
|---|---|---|---|
| 3,057,915 | 10/1962 | Riemenschneider et al. | 260/533 |
| 3,131,223 | 4/1964 | Smidt et al. | 260/597 |
| 3,240,805 | 3/1966 | Naglieri | 260/533 |
| 3,301,905 | 1/1967 | Riemenschneider et al. | 260/597 |
| 4,040,978 | 8/1977 | Li | 252/437 |
| 4,062,885 | 12/1977 | Mekhtiev et al. | 260/465 |
| 4,148,757 | 4/1979 | Brazdil et al. | 252/432 |
| 4,250,346 | 2/1981 | Young et al. | 585/658 |
| 4,339,355 | 7/1982 | Decker et al. | 252/464 |
| 4,405,498 | 9/1983 | Ebner | 252/432 |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,600,541 | 7/1986 | Aoki et al. | 558/321 |
| 4,899,003 | 2/1990 | Manyik et al. | 585/313 |
| 5,049,692 | 9/1991 | Hatano et al. | 558/319 |
| 5,162,578 | 11/1992 | McCain, Jr. et al. | 562/512.2 |
| 5,198,580 | 3/1993 | Bartek et al. | 562/542 |
| 5,300,682 | 4/1994 | Blum et al. | 562/512.2 |
| 5,688,739 | 11/1997 | Drenski et al. | 502/308 |

FOREIGN PATENT DOCUMENTS

| | | |
|---|---|---|
| 0 032 012 B1 | 7/1981 | European Pat. Off. . |
| 0 294 845 A1 | 12/1988 | European Pat. Off. . |
| 0 407 091 A1 | 1/1991 | European Pat. Off. . |
| 0 475 351 A1 | 3/1992 | European Pat. Off. . |
| 0 480 594 A2 | 4/1992 | European Pat. Off. . |
| 0 518 548 A2 | 12/1992 | European Pat. Off. . |
| 0 573 713 B1 | 12/1993 | European Pat. Off. . |
| 0 620 205 A1 | 10/1994 | European Pat. Off. . |
| 0 627 401 A1 | 12/1994 | European Pat. Off. . |

OTHER PUBLICATIONS

Thorsteinson, et al., "The Oxidative Dehydrogenation of Ethane over Catalysts Containing Mixed Oxides of Molybdenum and Vanadium" *Journal of Catalysis*, vol. 52, pp. 116–132 (1978).

*Primary Examiner*—Mark L. Bell
*Assistant Examiner*—Patricia L. Hailey
*Attorney, Agent, or Firm*—Whitman Breed Abbott & Morgan LLP

[57] ABSTRACT

An improved catalyst for the production of unsaturated nitrites from their corresponding olefins, the catalyst having the atomic ratios described by the empirical formula $Bi_a Mo_b V_c Sb_d Nb_e A_f B_g O_x$ and methods of using the same.

10 Claims, 1 Drawing Sheet

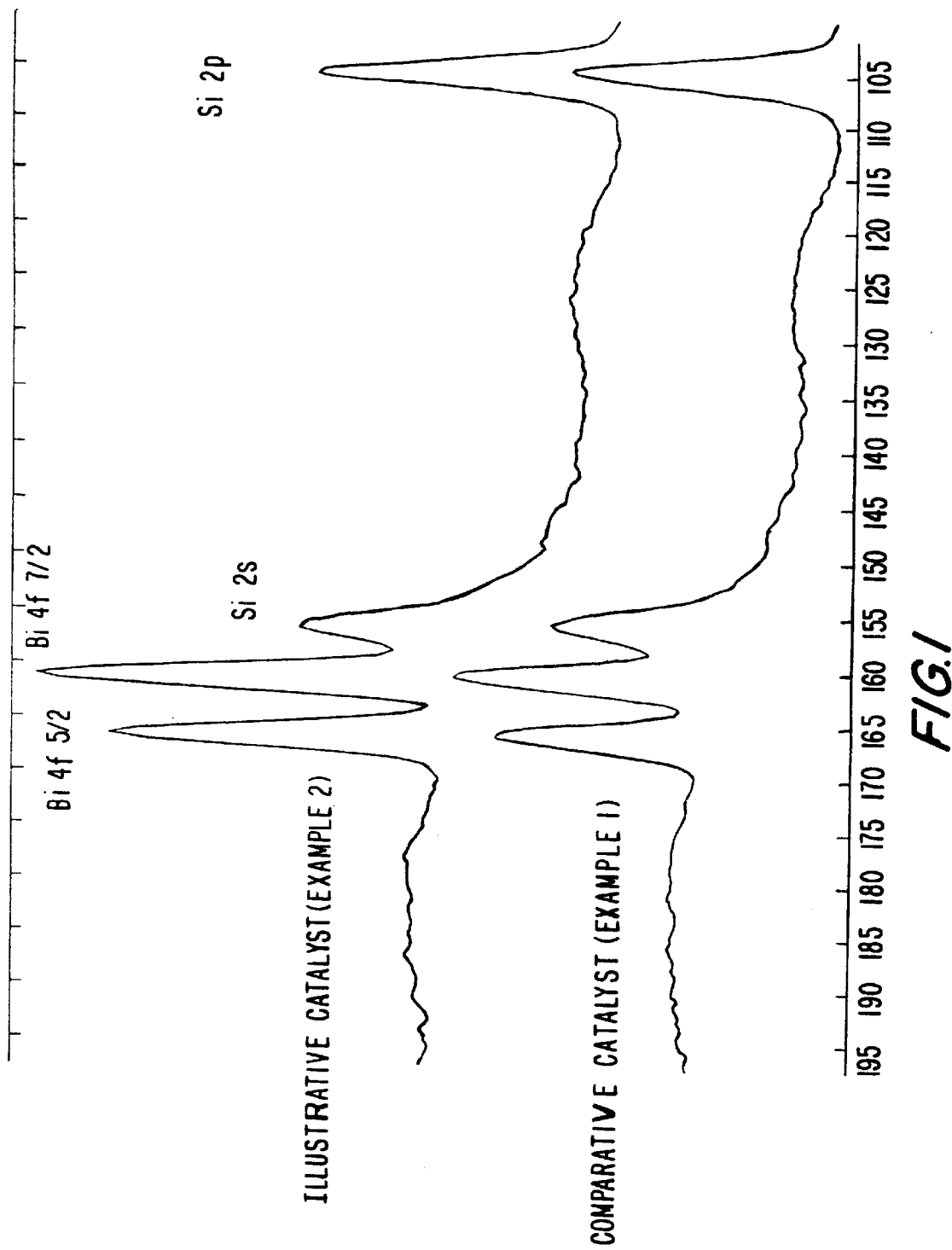

HIGHLY ACTIVE AND SELECTIVE CATALYSTS FOR THE PRODUCTION OF UNSATURATED NITRILES, METHODS OF MAKING AND USING THE SAME

BACKGROUND OF THE INVENTION

1. Field of the Invention

The present invention relates to new ammoxidation catalysts for the production of unsaturated nitriles from their corresponding olefins. More specifically, the present invention is directed to an improved ammoxidation catalyst containing niobium as an essential element for enhancing activity and selectivity of the catalyst system and methods of using the same.

2. Description of Related Art

Several publications are referenced in this application. The references describe the state of the art to which this invention pertains and are hereby incorporated by reference.

It is known in the art that the bismuth-molybdenum system plays a role in electron donor/acceptor mechanisms for selective oxidation and ammoxidation. Therefore different mechanisms have been proposed based on this property [Delmon et al. (New Development in Selective Oxidation by Heterogeneous Catalysis, Vol. 72, 1992, p. 399–413) and Encyclopedia of Chemical Technology (Kirk-Othmer, Vol. 1, 4th edition, page 358)]. In these mechanisms, molybdenum was shown to be responsible for oxygen and nitrogen uptake and insertion into the substrate, while bismuth plays the role of H-abstraction of the methyl group in the β position. Therefore, bismuth and molybdenum should be present on the catalyst surface and adjacent in order to form the suitable active phase for this reaction. It should be noted that the deficiency of bismuth on the catalyst surface leads to the total oxidation reaction of the substrate.

It is also well known that antimony plays the role of a donor and thus could improve the selectivity of the catalyst. Antimony can also play an additional role of isolating the vanadium active centers which are highly active towards the oxidation reaction. This leads to minimizing the total oxidation reaction and directs the reaction towards the desired product.

Many catalysts have been disclosed for the foregoing reactions. One such catalyst is described in U.S. Pat. No. 4,062,885, where BiMoSbV systems were used as active elements. The catalyst was used for the preparation of phthalonitrile by the ammoxidation of ortho-xylene. The use of such catalysts for oxidation or ammoxidation reactions involving unsaturated aliphatic hydrocarbons is not mentioned.

U.S. Pat. No. 4,040,978 relates to a catalyst for ammoxidation reactions containing bismuth molybdate mixed with other elements.

U.S. Pat. No. 4,405,498 relates to a catalyst for oxidation and ammoxidation reactions containing BiMoVSb with additional elements selected from groups IA, IIA, IVA, VA, VIA, IB, IVB and VIIB of the periodic Table of the Elements. Elements from group VB of the periodic table are not disclosed in this patent.

U.S. Pat. No. 4,600,541 relates to a catalyst comprising FeBiMo and promoters such as Pd, Pt, Os and Ir.

More recently, European Patent Publication No. 0 475 351 A1 relates to a catalyst containing KFeSbMo which could be promoted by Nb and W. The best yield was achieved with a catalyst of the formula $Fe_{10}Sb_{10}Mo_9Bi_2K_{0.6}Ni_{5.5}W_{0.3}B_{0.75}P_{0.75}$ $(SiO_2)_{70}$.

European Patent Publication No. 0 573 713 B1 relates to a catalyst comprising MoBiFeCoNiCr promoted with at least three other promoters selected from alkali metals, alkaline earth metals, rare earth metals, Nb, Tl and As, with Fe, Co, Ni and Cr as essential catalyst components.

U.S. Pat. No. 5,688,739 relates to a multi-component catalyst. The base of this catalyst is bismuth molybdenum. Germanium was added as an essential element. The use of niobium was not disclosed in this patent.

None of the prior art references discloses or suggests catalysts which provide high performance for the selective production of unsaturated nitrites from their corresponding olefins. Accordingly, it would be desirable to produce an improved catalyst for use in the selective production of unsaturated nitrites from their corresponding olefins.

OBJECTS OF THE INVENTION

It is an object of the invention to overcome the above-identified deficiencies.

It is another object of the invention to provide a useful, improved catalyst for the production of nitrites from their corresponding olefins, particularly for the production of acrylonitrile from propylene.

It is a further object of the invention to provide a process for the production of acrylonitrile at high yields by vapor phase catalytic ammoxidation of propylene in a fluidized or fixed bed reactor.

The foregoing and other objects and advantages of the invention will be set forth in or apparent from the following description.

SUMMARY OF THE INVENTION

The present invention relates to an improved catalyst for the production of unsaturated nitrites from their corresponding olefins, the catalyst having the atomic ratios described by the empirical formula set forth below:

$$Bi_aMo_bV_cSb_dNb_eA_fB_gO_x,$$

wherein

A=one or more elements selected from groups VB (e.g. V, Nb, Ta), VIB (e.g. Cr, Mo, W), VIIB (e.g. Mn, Tc, Re) or VIII (e.g. Fe, Co, Ni) of the periodic table;

B =at least one alkali promoter selected from groups IA (e.g., Li, Na, K) or IIA (e.g., Mg, Ca) of the periodic table;

a=0.01 to 12;

b=0.01 to 12;

c=0.01 to 2;

d=0.01 to 10;

e=0.01 to 1;

f=0 to 2, preferably from 0.01 to 1;

g=0 to 1, preferably from 0.001 to 0.5; and x=the number of oxygen atoms required to satisfy the valency requirements of the elements present.

The numerical values of a, b, c, d, e, f, g, and x represent the relative gram-atom ratios of the elements, respectively, in the catalyst, where x is a number required to satisfy the valence requirements of the other elements. The elements are present in combination with oxygen, preferably in the form of various oxides.

The invention also relates to an improved selective low temperature catalytic process for the production of nitrites from their corresponding olefins, particularly for the production of acrylonitrile from propylene.

Other objects as well as aspects, features and advantages of the present invention will become apparent from a study of the present specification, including the claims and specific examples.

BRIEF DESCRIPTION OF THE FIGURE

FIG. 1 is a graphical representation of photoelectron spectroscopy (XPS) patterns of a catalyst according to one embodiment of the invention and a comparative catalyst.

DESCRIPTION OF THE PREFERRED EMBODIMENTS

One aspect of the invention relates to an improved ammoxidation catalytic system for the production of unsaturated nitrites from their corresponding olefins, in particular, for the production of acrylonitrile from propylene. More specifically, the present invention is directed to an improved ammoxidation catalyst containing niobium as an essential element for enhancing activity and selectivity of the catalyst system. The aim of the present invention is to incorporate a new element into the Bi/Mo system which can improve the catalyst performance. This is achieved by incorporating niobium into a bismuth/molybdenum/vanadium/antimony catalyst system.

The improved ammoxidation catalytic system of the invention comprises the atomic composition described by the empirical formula set forth below:

$$Bi_aMo_bV_cSb_dNb_eA_fB_gO_x,$$

wherein

A=one or more elements selected from groups VB (e.g. V, Nb, Ta), VIB (e.g. Cr, Mo, W), VIIB (e.g. Mn, Tc, Re) or VIII (e.g. Fe, Co, Ni) of the periodic table;

B=at least one alkali promoter selected from groups IA (e.g., Li, Na, K) or IIA (e.g., Mg, Ca) of the periodic table;

a=0.01 to 12;
b=0.01 to 12;
c=0.01 to 2;
d=0.01 to 10;
e=0.01 to 1;
f=0 to 2, preferably from 0.01 to 1;
g=0 to 1, preferably from 0.001 to 0.5; and
x=the number of oxygen atoms required to satisfy the valency requirements of the elements present.

The catalysts of the invention can be used with or without a support. Suitable supports for the catalysts include alumina, silica, titania, zirconia, zeolites, silicon carbide, molecular sieves and other micro/nonporous materials, and mixtures thereof. When used on a support, the supported catalyst usually comprises from about 10 to 50% by weight of the catalyst composition, with the remainder being the support material.

Another aspect of the invention relates to methods of using the catalyst system of the invention. More specifically, the invention relates to an improved method of producing unsaturated nitrites from their corresponding olefins.

One preferred embodiment of the invention relates to an improved process for the catalytic preparation of acrylonitrile or metha acrylonitrile by the reaction of propylene or isobutylene with molecular oxygen and ammonia at a temperature of between about 200 to 600° C. using the ammoxidation catalytic system of the invention.

Preferably, the process achieves a propylene conversion of at least 65%, more preferably at least 70% and most preferred at least 75% using the catalytic system of the invention.

Preferably, the selectivity in mol % to acrylonitrile is greater than 80%, more preferably greater than 85%. The yield of acrylonitrile in mol % is preferably greater than 50%, more preferably greater than 55%, even more preferably greater than 60% and most preferred greater than 65%.

EXAMPLES

The following examples are illustrative of some of the catalysts and methods of making and using the same falling within the scope of the present invention. They are, of course, not to be considered in any way limitative of the invention. Numerous changes and modifications can be made with respect to the invention.

The basic catalyst of the present invention is a mixed metal oxide catalyst, which could be prepared according to any procedure well known by those skilled in the art. Methods used to prepare a catalyst with niobium as an essential element according to one embodiment of the invention and a comparative catalyst are given below. The catalysts were prepared by the methods described in U.S. Pat. No. 4,405,498, herein incorporated by reference.

As used in the following examples, the following terms are defined in the following manner:

1. "W/F" is defined as the weight of the catalyst in grams divided by the flow rate of the reactant stream in ml/sec measured at S.T.P.

2. "Propylene ($C_3H_6$) conversion" is defined as:

$$\frac{\text{Mols } C_3H_6 \text{ in feed} - \text{mols } C_3H_6 \text{ in effluent}}{\text{Mols } C_3H_6 \text{ in feed}} \times 100$$

3. "Acrylonitrile (ACN) selectivity" is defined as:

$$\frac{\text{Mols ACN in effluent}}{\text{Mols } C_3H_6 \text{ converted}} \times 100\%$$

4. "Acrylonitrile (ACN) yield" is defined as:

$$\frac{\text{Mols ACN formed}}{\text{Mols } C_3H_6 \text{ in feed}} \times 100\%$$

Example 1 (Comparative Catalyst): Bi MO $V_{0.175}Sb_{0.35}O_x$/50% Silica

Part A 10.2 g of $Sb_2O_3$ was slurried in 20ml water along with 3.18 g $V_2O_5$. The mixture was boiled until a paste was formed. The paste was then dried at 120° C. and calcined under airflow at 760° C. for 2 hrs.

Part B 97 g Bi(NO$_3$)$_3$ 5H$_2$O was dissolved in 184 ml water and 30 ml HNO$_3$ (concentrated). Separately, 28.78 g MoO$_3$ was dissolved in 72 ml water and 30 ml concentrated NH$_4$OH. The two solutions were mixed together and the pH was adjusted to 4 using NH$_4$OH. The mixture was then boiled ca. 2 hours, filtered and washed with ca. 1000 ml water.

Part C

The pH of 297 g of a silica solution 30 wt % was adjusted with HNO$_3$ to pH=2 to form Part C. Parts A and B were then added to Part C. The mixture was stirred for several hours, then dried at 120° C. and calcined under airflow at 550° C. The resultant catalyst was characterized by means of an XPS technique. The results are shown in FIG. 1.

Example 2: Bi Mo Nb$_{0.1}$ V$_{0.175}$ Sb$_{0.35}$ O$_x$/50% Silica

This catalyst was prepared according to the above described method set forth in Example 1. Niobium was introduced to the system using the required amount of niobium pentaoxide added to the molybdenum solution in part B. However, any source of niobium could be used for the same purpose.

The catalyst was characterized by means of an XPS technique. The results are shown in FIG. 1.

Catalyst Test

The calcined catalysts of Examples 1 and 2 were crushed to 35–60 mesh fraction. 5 g of each catalyst were charged into a tubular fixed bed stainless steel reactor.

The reaction was carried out under 475° C. at atmospheric pressure with the following feed composition: propylene/O$_2$/NH$_3$/He=7.9/16.8/10/65.3 and a space velocity "W/F" of 3.

Comparison

The catalysts of Example 1 and Example 2 were tested under the similar conditions listed above.

After reaching the steady state, the reactor effluents were analyzed using a modern gas chromatograph (HP 6890), equipped with both FID and TCD detectors. HCN was collected for a given period of time and then titrated.

Activity results were calculated according to the equations given above. Results are summarized in the following table.

parative catalyst of Example 1. The selectivity was significantly enhanced at the cost of total oxidation and HCN formation.

The activity and selectivity improvement is believed to be attributed to the catalyst surface enrichment with bismuth as a result of niobium introduction to the system. This is demonstrated in the XPS results shown in FIG. 1.

The above description of the invention is intended to be illustrative and not limiting. Various changes or modifications in the embodiments described may occur to those skilled in the art. These can be made without departing from the spirit or scope of the invention.

What is claimed is:

1. A catalyst system for the production of unsaturated nitriles from the corresponding olefins comprising a catalyst having the empirical formula:

$$Bi_aMo_bV_cSb_dNb_eA_fB_gO_x,$$

wherein
A=one or more elements from groups VB, VIB, VIIB or VIII of the periodic table;
B=at least one alkali or alkaline earth metal promoter selected from groups IA or IIA of the periodic table;
a=0.01 to 12;
b=0.01 to 12;
c=0.01 to 2;
d=0.01 to 10;
e=0.01 to 1;
f=0 to 1;
g=0 to 0.5; and
x=the number of oxygen atoms required to satisfy the valency requirements of the elements present.

2. The catalyst system of claim 1, wherein e is from 0.05 to 0.5.

3. The catalyst system of claim 1, wherein said olefins are selected from propylene, isobutylene or mixtures thereof and said nitrites are selected from acrylonitrile, methacrylonitrile or mixtures thereof.

4. The catalyst system of claim 1, wherein said oxide catalyst is supported on a catalyst support material selected from silica, alumina, zirconia, titania, alundum, silicon carbide, alumina-silica, inorganic phosphates, silicates, aluminates, borates and carbonates, pumice, montmorillonite, or mixtures thereof.

5. The catalyst system of claim 4, wherein said catalyst support material is silica.

TABLE I

|  | Propylene Conversion | ACN | | ACCN | | ACROLEIN | | CO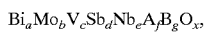 | | HCN | |
| --- | --- | --- | --- | --- | --- | --- | --- | --- | --- | --- | --- |
|  |  | Y | S | Y | S | Y | S | Y | S | Y | S |
| Example 1 | 62.9 | 48.7 | 77.5 | 3.1 | 4.9 | 0 | 0 | 10.0 | 16.0 | 0.6 | 0.9 |
| Example 2 | 77.4 | 67.9 | 87.7 | 2.6 | 3.4 | 0.9 | 1.1 | 5.3 | 6.9 | 0.3 | 0.3 |

ACN: Acrylonitrile
ACCN: Acetonitrile
HCN: Hydrogen cyanide
Y: Yield in mol %
S: Selectivity in mol %

As shown in the above Table I, the activity of catalyst of Example 2 (containing niobium) is higher than the com- 6. The catalyst system of claim 5, wherein the supported catalyst comprises from about 10 –50% by weight of the catalyst, with remainder being the support material.

7. The catalyst system of claim 4, wherein the supported catalyst comprises from about 10–50% by weight of the catalyst, with the remainder being the support material.

8. The catalyst system of claim 1, wherein said catalyst contains niobium derived from niobium pentoxide soluble in water.

9. The catalyst system of claim 1, wherein f ranges from 0.01 to 1 and g ranges from 0.001 to 0.5.

10. The catalyst of claim 1, wherein said catalyst contains niobium derived from a niobium source soluble in water.

* * * * *